United States Patent [19]

Johansson et al.

[11] Patent Number: 4,754,877

[45] Date of Patent: Jul. 5, 1988

[54] WETTING AND STORAGE DEVICE FOR A CATHETER

[75] Inventors: Eva G. Johansson, Göteborg; Jan M. R. Utas-Sjöberg, Mölndal, both of Sweden

[73] Assignee: Astra Meditec Aktiebolag, Mölndal, Sweden

[21] Appl. No.: 6,673

[22] PCT Filed: Apr. 28, 1986

[86] PCT No.: PCT/SE86/00191

§ 371 Date: Dec. 3, 1986

§ 102(e) Date: Dec. 3, 1986

[87] PCT Pub. No.: WO86/06284

PCT Pub. Date: Nov. 6, 1986

[30] Foreign Application Priority Data

Apr. 30, 1985 [SE] Sweden ............... 8502109

[51] Int. Cl.$^4$ ............................................. B65D 85/20
[52] U.S. Cl. ..................................... 206/364; 206/438; 383/38
[58] Field of Search .............. 206/364, 210, 570, 571, 206/572, 219, 438, 439; 128/763, 767, 768; 604/171, 172, 199; 383/37, 38, 39, 40

[56] References Cited

U.S. PATENT DOCUMENTS

| | | | |
|---|---|---|---|
| 3,064,800 | 11/1962 | Hart | 206/445 |
| 3,403,776 | 10/1968 | Denny | 206/363 |
| 3,674,195 | 7/1972 | Stone | 206/632 |
| 3,730,337 | 5/1973 | White | 206/484 |
| 3,794,042 | 2/1974 | De Klotz et al. | 604/171 |
| 3,926,309 | 12/1975 | Center | 206/364 |
| 3,954,174 | 5/1976 | Kraus | 206/439 |
| 3,958,750 | 5/1976 | Prybeck | 383/38 |
| 4,091,922 | 5/1978 | Egler | 604/171 |
| 4,366,901 | 1/1983 | Short | 206/364 |
| 4,417,612 | 11/1983 | Couture et al. | 383/39 |

FOREIGN PATENT DOCUMENTS

| | | |
|---|---|---|
| 2317839 | 10/1974 | Fed. Rep. of Germany . |
| 2447328 | 9/1980 | France ........... 383/40 |
| 439110 | 8/1985 | Sweden . |

Primary Examiner—Jimmy G. Foster
Attorney, Agent, or Firm—Brumbaugh, Graves, Donohue & Raymond

[57] ABSTRACT

At intermittent self catheterization it is, for a wider use of the method, desirable to enable repeated use of a catheter, preferably a limited number of times. This applies also to surface coated catheters having low friction in wet condition (LoFric ®). For this purpose the invention provides a wetting and storage device for a catheter, which device comprises an elongated carrying strip (1) provided with means for retaining a catheter. The device is characterized in that, along one side of said strip there is arranged a wetting pocket (2) closed at one end thereof in which a liquid (6) may be filled and in which a catheter (7) may be introduced for wetting thereof, and that on said strip there is further arranged at least one sheet (8,9,27) of porous material, under which a catheter may be put in for drying and storage. By providing the device with a number of tablets (5) (e.g. 3-6 tablets), of which one, according to an instruction, is to be dissolved in the liquid (6) at each occasion of use, one may induce a recommended number of use occasions for a catheter.

11 Claims, 2 Drawing Sheets

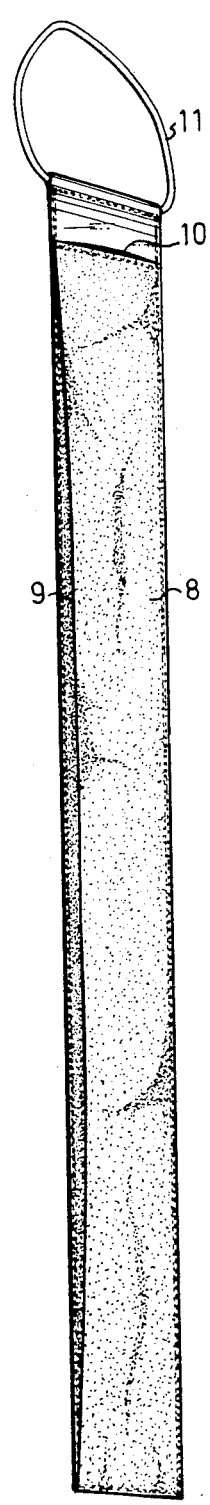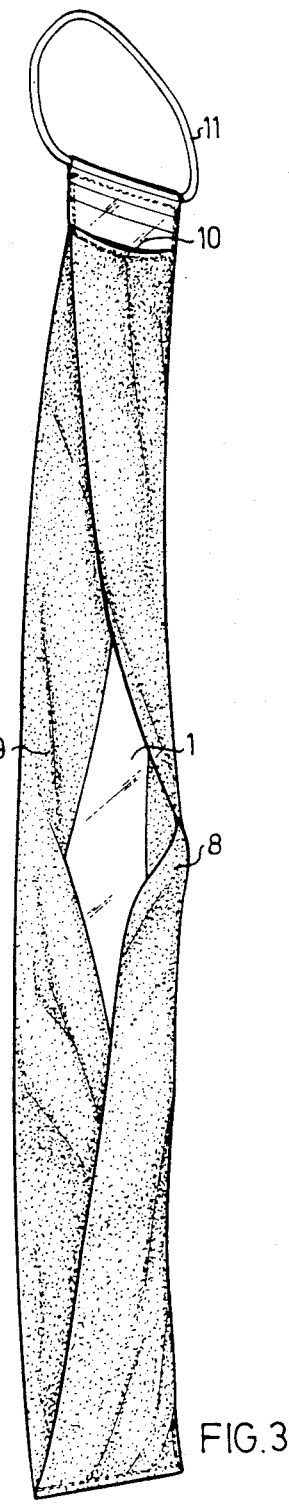

WETTING AND STORAGE DEVICE FOR A CATHETER

TECHNICAL FIELD

The present invention is related to a wetting and storage device for a catheter.

With certain categories of patients intermittent self catheterization is employed. An indwelling catheter is inconvenient to the patient and is connected with risks for damage to the urinary bladder and infections. It has been found that intermittent catheterization does away with many problems, in particular when it can be carried out by the patient. For example, with patients having certain strictures or traumas in the urinary system as well as with paralysed patients a nearly normal home living is made possible by the patient learning how to insert a catheter into the urethra and draw off urine, as required a number of times per day, whereupon the catheter is removed. A significant aid for such patients is the provision of surface coated catheters having low friction in wet condition, e.g. LoFric ®. Whether conventional catheters or surface coated catheters are employed, it has hitherto been necessary for hygienic reasons to consume one catheter at each catheterization. This is however so costly that there is a risk that the method will not be very widely employed. It is thus desirable to enable a repeated use of a catheter. However, neither hygiene nor other properties of the catheter can be guaranteed if use is repeated substantially above a recommended number of use occasions.

An object of the present invention is to achieve a device enabling repeated use of a catheter, and preferably a device arranged in such way that a limited number of uses is induced. Other objects will be evident from the description below.

DESCRIPTION OF THE INVENTION

According to the present invention there is provided a wetting and storage device for a catheter, which device comprises an elongated carrying strip provided with means for retaining a catheter. The device is characterized in that on one side of said strip there is arranged a wetting pocket closed at one end thereof, in which wetting pocket liquid may be filled and a catheter may be introduced for wetting thereof, and that on said strip there is further arranged at least one sheet, under which a catheter may be put in for storage.

According to one embodiment of the invention the sheet(s) under which a catheter may be put in for drying and storage is at least one flap of porous material on the other side of the carrying strip.

The device according to the invention may be held in a vertical position thus that the liquid may be filled into the wetting pocket and the catheter introduced therein. Preferably the carrying strip has means for suspension thereof at the end thereof proximal to the opening of the wetting pocket.

After use, the catheter may be put in under flaps of porous material on the other side of the strip. These flaps are preferably in the shape of two strips, each attached along one long edge of the carrying strip and overlapping each other.

With such surface coated catheters which have low friction in wet condition the lowering of friction is obtained by wetting in water, whereby it is usually required an addition of common salt and possibly bactericidal compounds and other additives to the water.

According to a preferred embodiment of the invention the device has a space for holding a number of tablets. Said tablets are intended to be dissolved by the liquid after filling of the wetting pocket. By a tablet is meant herein, in addition to a compressed tablet, any other body comprising a substance which may be dissolved in the liquid, such as a capsule with solid or liquid contents. An especially preferred tablet is however a compressed effervescent tablet produced in a manner known per se in drug industry.

According to an especially preferred embodiment of the invention the tablets belonging to the device are placed in an additional pocket. According to an alternative preferred embodiment of the invention the tablets are placed within the wetting pocket of the device, individually enclosed in a liquid-tight protective package from which the tablets may be individually released. Thus, one may, preferably by manipulating the device from the outside, break the protective package for a tablet in such way that said tablet is released into the liquid package and dissolved on filling of the liquid. By providing the device with a given number of tablets (e.g. 3–6 tablets), of which according to an instruction, one is to be dissolved at each occasion of use, one may induce a recommended number of use occasions for a catheter equal to the number of tablets. Irrespective of how the tablets are placed in the device they may be enclosed in a package known per se, such as a foil or blister pack.

When desired, and in particular with conventional catheters having no surface coating, the tablets may comprise a lubricant which after dissolution in the liquid and wetting of the catheter facilitates introduction of the catheter in the urethra.

DETAILED DESCRIPTION OF THE INVENTION

Reference is made to the enclosed drawings wherein

Figure 1:
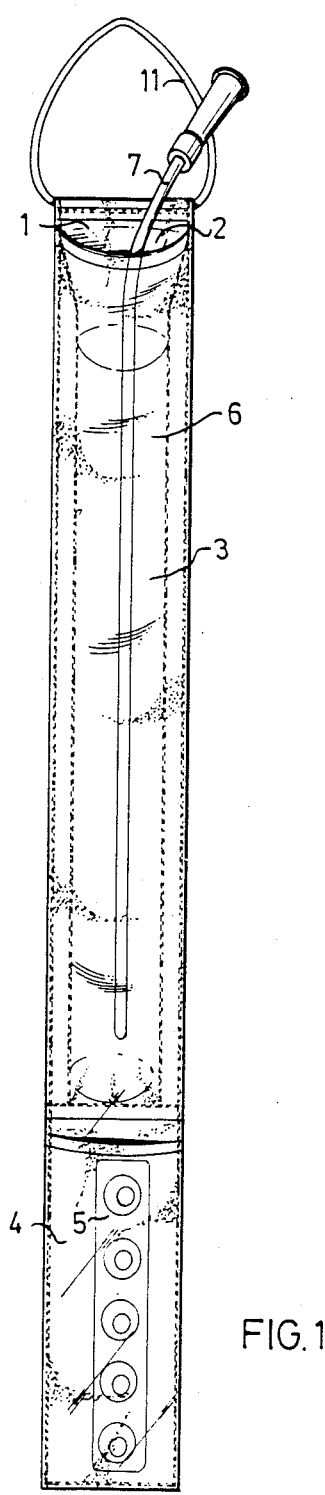
Figure 4:
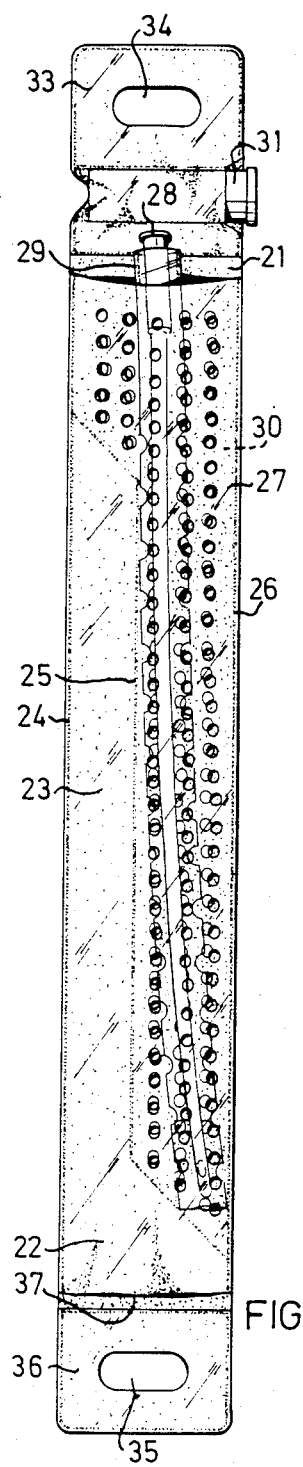

FIG. 1 shows a device according to the invention viewed from the side of the wetting pocket with a tablet pack and a catheter, FIG. 2 shows a device according to the invention viewed from the side opposite to the wetting pocket, FIG. 3 shows the device of FIG. 2 from the same direction with separated flaps, and FIG. 4 shows a device according to a further embodiment of the invention.

The device of FIGS. 1–3 comprises a carrying strip 1, usually made of plastic foil material. A wetting pocket 2 is arranged by a second strip 3 being heat sealed to the carrying strip along the long edges and one short edge thereof, being in use position the lower short edge. A second pocket 4 is arranged in a similar manner on the same side of the carrying strip and contains a tablet pack 5 with five tablets. The wetting pocket is filled to a desired level with a liquid 6, and a catheter 7 is in a lowered position therein for wetting thereof. The flaps of porous material 8, 9 arranged on the other side of the carrying strip are each heat sealed along each one long edge and one and the same short edge thereof. The flaps are joined with each other at their other short edge but are free from the carrying strip at said edge, thus that an opening 10 is formed through which the catheter may be introduced.

The catheter may be removed by separating the flaps 8 and 9 as shown in FIG. 3. The flaps are suitably made of textile material or textile-resembling porous material such as paper or polymer fibre material (Tyvek ®, Celgard ®). A suspension loop 11 is arranged at the end of the device proximal to the opening of the wetting pocket, which end is the upper end in use position. Said loop may alternatively be an extension of the carrying strip having a suspension hole therein.

In the device of FIG. 4 an elongated carrying strip 21 of foil material is provided on one side thereof with a wetting pocket 22 for a catheter arranged by heatsealing a sheet 23 of foil material to the carrying strip by heat sealing lines 24 and 25. Heat sealing lines 25 and 26 define a perforated portion 27 of said sheet under which a catheter 28 is put in for drying and storage. Said catheter is contained within an inner pocket 29 as delivered. Heat sealing lines 24 and 25 also define a perforated portion 30 of the carrying strip corresponding to portion 27. A tube 31 containing tablets is enclosed in an additional pocket 32 on an extension 33 at one end of the carrying strip. In said extension a first suspension hole 34 is arranged. A second suspension hole 35 is arranged in an extension 36 at the opposite end of the carrying strip for suspension of the device when the wetting pocket 22 is filled with liquid via opening 37.

The device of the FIGS. 1-3 is used in the following manner. A tablet is pressed out of the package thereof. This is done directly in the wetting pocket if the package is placed therein. Otherwise the tablet is dropped into the wetting pocket. The catheter is taken out by separating the flaps on the back of the device. The catheter is put down into the wetting pocket and water is filled up to a level mark. Dissolution of the tablet is awaited, whereupon the catheter is taken up and used for catheterization. After finishing catheterization the wetting pocket is emptied, the catheter is rinsed under running water and put back behind the flaps where it is dryed through the porosity of the flap material until the next occasion of use.

In use of the device of FIG. 4 the catheter 28 and inner pocket 29 are removed from its storage area under portion 27. The device is suspended at its second suspension hole 34. A tablet is removed from tube 31 and dropped into the wetting pocket 22. The catheter 28 and inner pocket 29 are introduced into the wetting pocket 22 which is subsequently or previously filled with water. The catheter and inner pocket are taken out and the catheter is removed from the inner pocket, whereupon catheterization takes place. Rinsing and replacement of the catheter under the perforated sheet takes place in an analogous manner to what is described above.

We claim:

1. A wetting and storage device for a catheter, comprising an elongated carrying strip (1) provided with means for retaining a catheter, said retaining means including a pocket affixed along one side of said strip, said pocket being closed at both sides and one end thereof and adopted to directly hold liquid (6) into which a catheter (7) may be introduced for wetting thereof, said retaining means also including at least one air permeable sheet (8,9,27) affixed along said strip and defining a receptacle into which a catheter may be put for drying and storage.

2. A wetting and storage device according to lcaim 1, characterized in that the sheet(s) defining the receptacle is at least one flap (8,9) of porous material on the other side of the carrying strip.

3. A wetting and storage device according to claim 2 characterized in that an additional pocket (4,32) is arranged along a portion of the carrying strip and a number of tablets (5) intended to be dissolved in the liquid (6) are received in the additional pocket.

4. A wetting and storage device according to claim 2, characterized in that a number of tablets intended to be dissolved in the liquid (6) are placed in the wetting pocket (2), ech individually enclosed in a liquid tight protective package from which the tablets may be individually released.

5. A wetting and storage device according to claim 2, characterized in that the flaps (8,9) made of porous material and placed on the other side of the carrying strip are in the shape of two strips, each attached along one long edge of the carrying strip (1) and overlapping each other.

6. A wetting and storage device according to claim 5 characterized in that an additional pocket (4,32) is arranged along a portion of the carrying strip and a number of tablets (5) intended to be dissoled in the liquid (6) are received in the additional pocket.

7. A wetting and storage device according to claim 5, characterized in that a number of tablets intended to be dissolved in the liquid (6) are placed in the wetting pocket (2), each individually enclosed in a liquid tight protective package from which the tablets may be individually released.

8. A wetting and storage device according to claim 1 characterized in that an additional pocket (4,32) is arranged along a portion of the carrying strip and a number of tablets (5) intneded to be disspolved in the liquid (6) are received in the additional pocket.

9. A wetting and storage device according to claim 8, characterized in that the number of tablets (5) is chosen in accordance with a recommended number of use occasions for a catheter.

10. A wetting and storage device according to claim 1, characterized in that a number of tablets intended to be dissolved in the liquid (6) are placed in the wetting pocket (2), each individually enclosed in a liquid tight protective package from which the tablets may be individually released.

11. A wetting and storage device according to claim 10, characterized in that the number of tablets (5) is chosen in accordance with a recommended number of use occasions for a cathether.

* * * * *